(12) United States Patent
Scarborough et al.

(10) Patent No.: US 7,361,669 B2
(45) Date of Patent: Apr. 22, 2008

(54) COMPOSITIONS AND METHOD FOR INHIBITING TGF-β

(75) Inventors: Robert M. Scarborough, Half Moon Bay, CA (US); Anjali Pandey, Fremont, CA (US); Mukund Mehrotra, South San Francisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 424 days.

(21) Appl. No.: 10/747,531

(22) Filed: Dec. 29, 2003

(65) Prior Publication Data

US 2004/0157861 A1 Aug. 12, 2004

Related U.S. Application Data

(60) Provisional application No. 60/437,679, filed on Jan. 2, 2003.

(51) Int. Cl.
*A61K 31/445* (2006.01)
(52) U.S. Cl. ...................................... 514/315
(58) Field of Classification Search ............... None
See application file for complete search history.

(56) References Cited

FOREIGN PATENT DOCUMENTS

| | | |
|---|---|---|
| EP | 0372445 B1 | 3/1994 |
| WO | WO 91/18885 A1 | 12/1991 |
| WO | WO 00/61576 A1 | 10/2000 |
| WO | WO 01/37835 A1 | 5/2001 |
| WO | WO 02/14311 A2 | 2/2002 |

OTHER PUBLICATIONS

Czarnocka-Janowicz, A. et al., "Synthesis and pharmacological activity of 5-substituted-s-triazole-3-thiols," *Pharmazie, Veb Verlag Volk Und Gesundheit*, vol. 46, No. 2 (1991), pp. 109-112.

*Primary Examiner*—Raymond J. Henley, III

(57) ABSTRACT

This invention provides compounds that are inhibitors of the TGF-β signaling pathway. The compounds are represented by formula I:

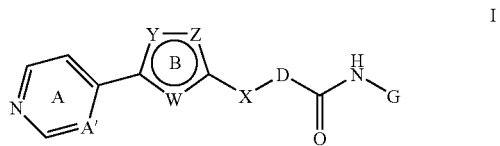

where A' is N or CH; Ring B is preferably an triazolyl, imidazolyl, or thiazolyl ring; —X-D- is a linker group; and G is an optionally substituted aryl or heteroaryl ring. The compounds are useful for treating cardiovascular disease.

7 Claims, No Drawings

COMPOSITIONS AND METHOD FOR INHIBITING TGF-β

This application claims the benefit under 35 U.S.C. § 119(e) of U.S. Provisional Application No. 60/437,679, filed Jan. 2, 2003.

FIELD OF INVENTION

This invention relates to novel methods of inhibiting the transforming growth factor (TGF)-β signaling pathway. The methods are particularly useful for treating cardiovascular disease.

BACKGROUND OF THE INVENTION

TGF-β1 belongs to a large super-family of multifunctional polypeptide factors. The TGF-β family includes three genes, TGFβ1, TGFβ2 and TGFβ3, which are pleiotropic modulators of cell growth and differentiation, embryonic and bone development, extracellular matrix formation, hematopoiesis, immune and inflammatory responses. These genes have high homology with one another. In mammals, the TGFβ super-family includes various TGFβ genes, as well as the embryonic morphogens, such as the family of the activins, inhibins, "Mullerian Inhibiting Substance", and bone morphogenic protein (BMP). Roberts and Sporn, The Transforming Growth Factor-βs in Peptide Growth Factors and Their Receptors. I. *Handbook of Experimental Pharmacology*, vol. 95/I, Springer-Verlag, Berlin, 419-472 (1990). Each member of the TGF-β family exerts a wide range of biological effects on a large variety of cell types, e.g., they regulate cell growth, morphogenesis, differentiation, matrix production and apoptosis. Lagna et al., *Nature*, 383:832-836 (1996). TGF-β acts as a growth inhibitor for many cell types and appears to play a central role in the regulation of embryonic development, tissue regeneration, immuno-regulation, as well as in fibrosis and carcinogenesis. TGFβ1 inhibits the growth of many cell types, including epithelial cells, but stimulates the proliferation of various types of mesenchymal cells.

In addition, TGFβs induce the synthesis of extracellular matrix (ECM) proteins, modulate the expression of matrix proteinases and proteinase inhibitors and change the expression of integrins. ECM is a dynamic superstructure of self aggregating macromolecules including fibronectin, collagen and proteoglycan. ECM is the chief pathologic feature of fibrotic diseases. ECM disorder has been proposed to play a central role in pathogenesis disorders such as hypertensive vascular disease and diabetic renal disease. Sato et al., *Am. J. Hypertens.*, 8:160-166 (1995); Schulick et al., *Proc. Natl.Acad.Sci.*, 95:6983-6988 (1988). Moreover, TGFβs are expressed in large amounts in many tumors. Derynck, *Trends Biochem. Sci.*, 19:548-553, (1994). This strong occurrence in neoplastic tissues could indicate that TGFβs are strategic growth/morphogenesis factors which influence the malignant properties associated with the various stages of the metastatic cascade. TGFβs inhibit the growth of normal epithelial and relatively differentiated carcinoma cells, whereas undifferentiated tumor cells which lack many epithelial properties are generally resistant to growth inhibition by TGFβs (Hoosein et al., Exp. Cell. Res. 181:442-453 (1989); Murthy et al., *Int'l J. Cancer*, 44:110-115 (1989). Furthermore TGFβ1 may potentiate the invasive and metastatic potential of a breast adenoma cell line (Welch et al., *Proc. Natl. Acad. Sci.*, 87:7678-7682 (1990), which indicates a role of TGFβ1 in tumor progression. The molecular mechanisms underlying the effect of TGFβs during tumor cell invasion and metastasization do, however, require further explanation.

The cellular effects of TGF-β are exerted by ligand-induced hetero-oligomerization of two distantly related type I and type II serine/threonine kinase receptors, TGF-βR-I and TGF-β R-II, respectively. Lin and Lodish, *Trends Cell Biol.*, 11:972-978. (1993); Massague and Weis-Garcia, *Cancer Surv.*, 27:41-64 (1996); ten Dijke etal., *Curr. Opin. Cell Biol.*, 8:139-145 (1996). The two receptors, both of which are required for signaling, act in sequence; TGF βR-I is a substrate for the constitutively active TGF-βR-II kinase. Wrana et al., *Nature*, 370:341-347 (1994); Wieser et al., *EMBO J.*, 14:2199-2208 (1995). Upon TGF-β1 binding, the type II receptor phosphorylates threonine residues in GS domain of ligand occupied type 1 receptor or activin like kinase. (ALK5) which results in activation of type I receptors. The TGF-β1 type I receptor in turn phosphorylates Smad2 and Smad3 proteins which translocate to the nucleus and mediate intracellular signaling. The inhibition of ALK5 phosphorylation of Smad3 will reduce TGF-β1 induced extracellular matrix production. Krettzchmar et al., *Genes Dev.*, 11: 984-995 (1997); Wu et al., *Mol. Cell. Biol.*, 17:2521-2528 (1997).

TGF-β is a powerful and essential immune regulator in the vascular system capable of modulating inflammatory events in both leuko and vascular endothelial cells. Shull et al., *Nature*, 359:693-699 (1992). It is also involved in the pathogenesis of chronic vascular diseases such as atherosclerosis and hypertension. Grainger & Metcalfe et al., *Bio. Rev. Cambridge Phil. Soc.*, 70:571-596 (1995); Metcalfe et al., *J. Human Hypertens.*, 9:679 (1995).

Genetic studies of TGF-β-like signaling pathways in i Drosophila and *Caenorhabditis elegans* have led to the identification of mothers against dpp (Mad). Sekelsky et al., *Genetics*, 139:1347-1358 (1995) and sma genes respectively. Savage et al., *Proc. Natl. Acad. Sci. USA*, 93:790-794, (1996). The products of these related genes perform essential functions downstream of TGF-β-like ligands acting via serine/threonine kinase receptors in these organisms. Wiersdorf et al., *Development*, 122:2153-2163 (1996); Newfeld et al., Development, 122:2099-2108 (1996); Hoodless et al., *Cell*, 85:489-500 (1996). Vertebrate homologs of Mad and sma have been termed Smads. Derynck et al., *Cell*, 87:173 (1996) or MADR genes. Wrana and Attisano, *Trends Genet.*, 12:493-496 (1996). SMAD proteins have been identified as signaling mediators of TGF-β superfamily. Hahn et al., *Science*, 271:350-353 (1996). Genetic alterations in Smad2 and Smad4/DPC4 have been found in specific tumor subsets, and thus Smads may function as tumor suppressor genes. Hahn et al., *Science*, 271:350-353 (1996); Riggins et al., *Nature Genet.*, 13:347-349 (1996); Eppert et al., *Cell*, 86:543-552 (1996). Smad proteins share two regions of high similarity, termed MH1 and MH2 domains, connected with a variable proline-rich sequence. Massague, *Cell* , 85:947-950 (1996); Derynck and Zhang, *Curr. Biol.*, 6:1226-1229 (1996). The C-terminal part of Smad2, when fused to a heterologous DNA-binding domain, was found to have transcriptional activity. Liu et al., *Nature*, 381:620-623 (1996); Meersseman et al., *Mech. Dev.*, 61:127-140 (1997). The intact Smad2 protein when fused to a DNA-binding domain, was latent, but transcriptional activity was unmasked after stimulation with ligand. Liu et al., supra.

TGF-β initiates an intracellular signaling pathway leading ultimately to the expression of genes that regulate the cell cycle, control proliferative responses, or relate to extracellular matrix proteins that mediate outside-in cell signaling, cell adhesion, migration and intercellular communication.

There exists a need for effective therapeutic agents for inhibiting TGF-β activity, as well as for inhibiting the phosphorylation of smad2 or smad3 by TGF-β type I or activin like kinase (ALK)-5 receptor and for preventing and treating disease states mediated by the TGF-β signaling pathway in mammals. In particular, there continues to be a need for compounds which selectively inhibit TGF-β.

DETAILED DESCRIPTION OF THE INVENTION

The present invention provides methods for treating patients having TGF-β mediated disorders, particularly cardiovascular disease. The method comprises administering a therapeutically effective amount of a compound of formula I:

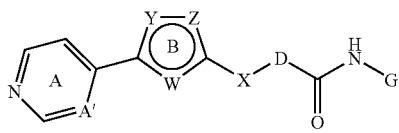

or a pharmaceutically acceptable salt thereof, wherein:
A' is N or CH;
Ring A is optionally substituted by 1-3 $R^1$;
Ring B is a heteroaryl ring that is optionally substituted at a substitutable nitrogen by $R^3$ and optionally substituted at a substitutable carbon by $R^{2a}$, wherein (a) W is NH, Z is N, and Y is CH, (b) W is NH, Z is N, and Y is N, (c) W is NH, Z is CH, and Y is N, (d) W is CH, Z is NH, and Y is N, (e) W is S, Z is N, and Y is CH, (f) W is S, Z is N, and Y is N, (g) W is S, Z is CH, and Y is N, (h) W is O, Z is N, and Y is CH, (i) W is N, Z is O, and Y is CH, or (j) W is N, Z is S, and Y is CH;
—X-D- is a linker group having a length of about 300 to 900 picometers;
G is an aryl or heteroaryl ring that is optionally substituted by 1-4 $R^5$;
each $R^1$ is independently selected from —$R^2$, -T-$R^2$, or —V-T-$R^2$;
each $R^2$ is independently selected from $C_{1-3}$ aliphatic, hydroxy, —$N(R^3)_2$, halo, cyano, —$OR^4$, —$C(O)R^4$, —$CO_2R^4$, —$SR^4$, —$S(O)R^4$, —$SO_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, phenyl, 5-6 membered heterocyclyl or 5-6 membered heteroaryl;
$R^{2a}$ is $C_{1-6}$ alkyl;
each T is independently a $C_{1-5}$ alkylidene that is optionally interrupted by —O—, —C(O)—, —S—, —S(O)—, —$SO_2$—, or —$N(R^3)$—;
each V is independently selected from —O—, —S—, —S(O)—, —$SO_2$—, —C(O)—, —$N(R^3)$—, —$N(R^3)C(O)$—, or —$N(R^3)CO_2$—, —$N(R^3)SO_2$—, —$C(O)N(R^3)$—, —$SO_2N(R^3)$—, —$N(R^3)C(O)N(R^3)$—, or —$OC(O)$—;
each $R^3$ is independently selected from hydrogen, $C_{1-6}$ aliphatic, —$C(O)R^4$, —$CO_2R^4$, —$SO_2R^4$, or two $R^3$ on the same nitrogen together with their intervening nitrogen form a 5-6 membered heterocyclyl or heteroaryl ring having 1-3 ring heteroatoms selected from N, O, or S;

$R^4$ is a $C_{1-6}$ aliphatic group;
each $R^5$ is independently selected from —$R^6$, -Q-$R^6$, or —V-Q-$R^6$;
each Q is independently a $C_{1-5}$ alkylidene that is optionally interrupted by —O—, —C(O)—, —S—, —S(O)—, —$SO_2$—, or —$N(R^3)$—; and
each $R^6$ is independently selected from $C_{1-3}$ aliphatic, hydroxy, —$N(R^3)_2$, halo, cyano, —$OR^4$, —$C(O)R^4$, —$CO_2R^4$, —$SR^4$, —$S(O)R^4$, —$SO_2R^4$, —$N(R^3)C(O)R^4$, or —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, phenyl, 5-6 membered heterocyclyl or 5-6 membered heteroaryl.

The term "aliphatic" as used herein means straight-chain, branched or cyclic $C_1$-$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The terms "alkyl", "alkoxy", "hydroxyalkyl", "alkoxyalkyl", and "alkoxycarbonyl", used alone or as part of a larger moiety, include both straight and branched chains containing one to twelve carbon atoms. The terms "alkenyl" and "alkynyl", used alone or as part of a larger moiety, include both straight and branched chains containing two to twelve carbon atoms. The term "cycloalkyl, used alone or as part of a larger moiety, includes cyclic $C_3$-$C_{12}$ hydrocarbons which are completely saturated or which contain one or more units of unsaturation, but which are not aromatic.

The terms "haloalkyl", "haloalkenyl" and "haloalkoxy", mean alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2-pyrrolyl), NH (as in pyrrolidinyl) or NR$^+$ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —SO$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, —(CH$_2$)$_y$NHC(O) CH(V—R°)(R°); wherein each R° is independently selected from hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0-6; and V is a linker group. Examples of substituents on the aliphatic group or the phenyl ring of R° include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon 20 of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R$^+$, —N(R$^+$)2, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein each R$^+$ is independently selected from hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

Compounds of this invention may exist in alternative tautomeric forms, as exemplified by tautomers i and ii shown below. Unless otherwise indicated, the representation of any tautomer is meant to include all tautomeric forms.

Ring A may be a pyridinyl ring (A' is CH) or a pyrimidinyl ring (A' is N) as shown in II and III below:

wherein Y, Z, W, X, D and G are as defined above. Ring A is unsubstituted or substituted by 1-3 $R^1$ groups selected from —$R^2$, -T-$R^2$, or —V-T-R . V is preferably —O— or —NH—; T is preferably a $C_{1-5}$ alkylidene, more preferably $C_{2-4}$ alkylidene; and $R^2$ is preferably $C_{1-4}$ alkyl, $C_{1-3}$ alkoxy, amino, mono- or dialkylamino, or a 5-6 membered heterocyclyl or heteroaryl ring having 1-3 ring heteroatoms selected from N, O, or S. When $R^2$ is a mono- or dialkylamino, the alkyl groups are preferably independently selected from $C_{1-4}$ alkyl groups. Preferred $R^2$ rings include piperidinyl, piperazinyl, morpholinyl, or pyrrolidinyl rings.

Preferred positions for substitution on Ring A are at the 2- and/or 6-positions. One embodiment of this invention relates to compounds of formula IV below:

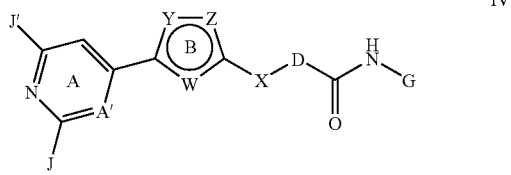

where J and J' are each independently selected from hydrogen or $R^1$ where $R^1$, T, V, W, Z, X, D and G are as described above. Preferably J and J' are each independently selected from hydrogen, —N($R^3$)$_2$, -T-N($R^3$)$_2$, or —V-T-N($R^3$)$_2$.

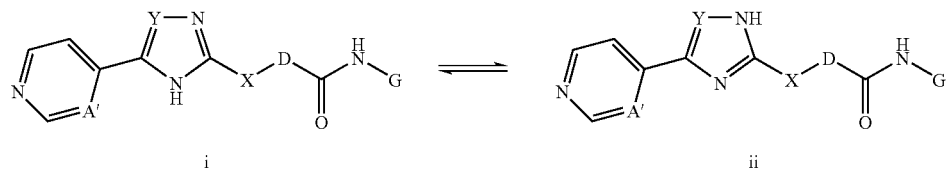

Ring B is preferably selected from the following:

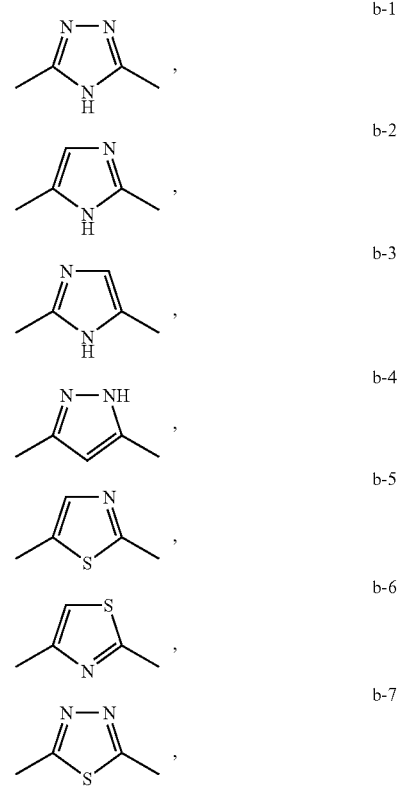

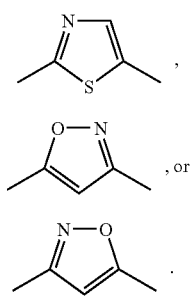

More preferred Ring B moieties are b-1, b-2, b-3, b-5 and b-6. Even more preferred are rings b-1, b-2, b-5 and b-6.

One embodiment of the invention relates to compounds where Ring A is a pyridyl and Ring B is an imidazolyl, triazolyl or thiazolyl as shown by II-B1, II-B2, II-B3, II-B5, II-B6 and II-B7:

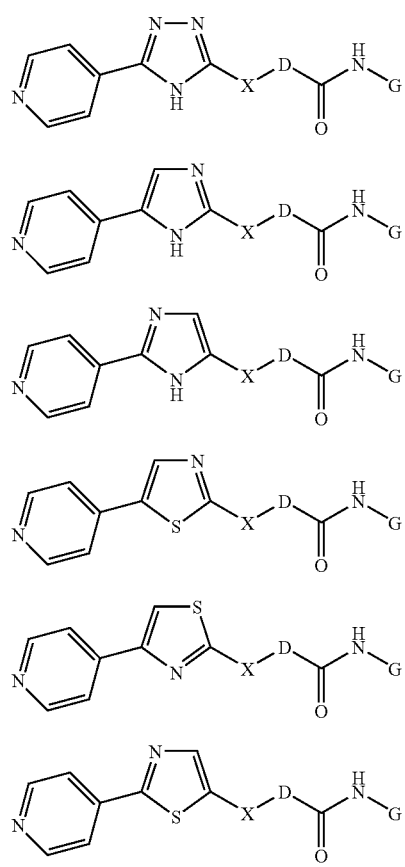

where X, D, and G are as defined above. Another embodiment relates to the use of a compound of formula II-B1, II-B2, II-B5 or II-B6.

The —X-D- moiety is a linker group that separates Ring B and the C(=O)NH-G moiety in compounds of formula I. The distance between Ring B and C(=O)NH-G is approximately the length of a 2-6 linear carbon chain or between about 300 to 900 picometers (pm). Preferably the distance is that of a 2-4 carbon chain, more preferably that of a 2-3 carbon chain or 300 to 450 pm. The optimal distance between Ring B and C(=O)NH-G may also be obtained by replacing one or more methylene units of an alkylidene linker with other groups such as —O—, —S—, —N($R^7$)CO—, —N($R^7$)CO$_2$—, —CON($R^7$)—, —CO—, —CO$_2$—, —OC(=O), —OC(=O)N($R^7$)—, —SO$_2$—, —N($R^7$)SO$_2$—, or —SO$_2$N($R^7$)— where $R^7$ is preferably hydrogen or an alkyl group. Alternatively, the alkylidene chain may constrained as part of a 3-7 membered ring. One skilled in the art will be able to select a suitable —X-D-linker by reference to the known bond distances of various atom pairs and/or ring systems in light of the examples presented below. A preferred —X— component of the linker is —S—, —O—, —NH—, —N(CH$_3$)— or —CH$_2$—. The -D- component is preferably a 1-3 carbon alkylidene chain that is substituted or unsubstituted. Examples of suitable substituents on -D- include $C_{1-4}$ alkyl, halo, oxo, and $C_{1-4}$ alkoxy. A preferred -D- component is —CH$_2$— or —CH$_2$CH$_2$—.

A preferred embodiment of the invention relates to compounds where Ring B is triazolyl, imidazolyl, or thiazolyl, —X-D- is —X—CH$_2$—, and —X— is —S—, —O—, —NH— or —CH$_2$—. Ring A may be substituted or unsubstituted. Compounds of this embodiment, exemplified where Ring A is unsubstituted, are shown in Table 1.

TABLE 1

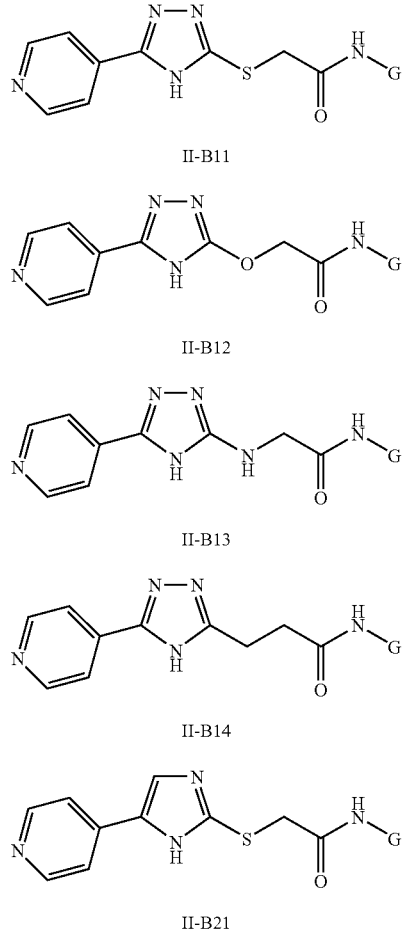

TABLE 1-continued

II-B22

II-B23

II-B24

II-B31

II-B32

II-B33

II-B34

II-B51

II-B52

II-B53

II-B54

II-B61

II-B62

II-B63

II-B64

II-B71

II-B72

TABLE 1-continued
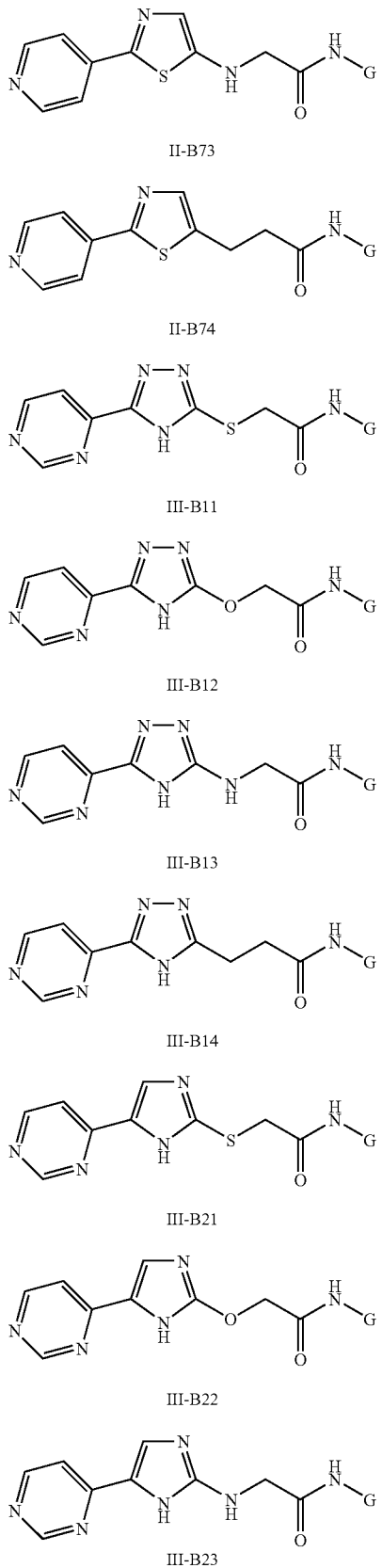
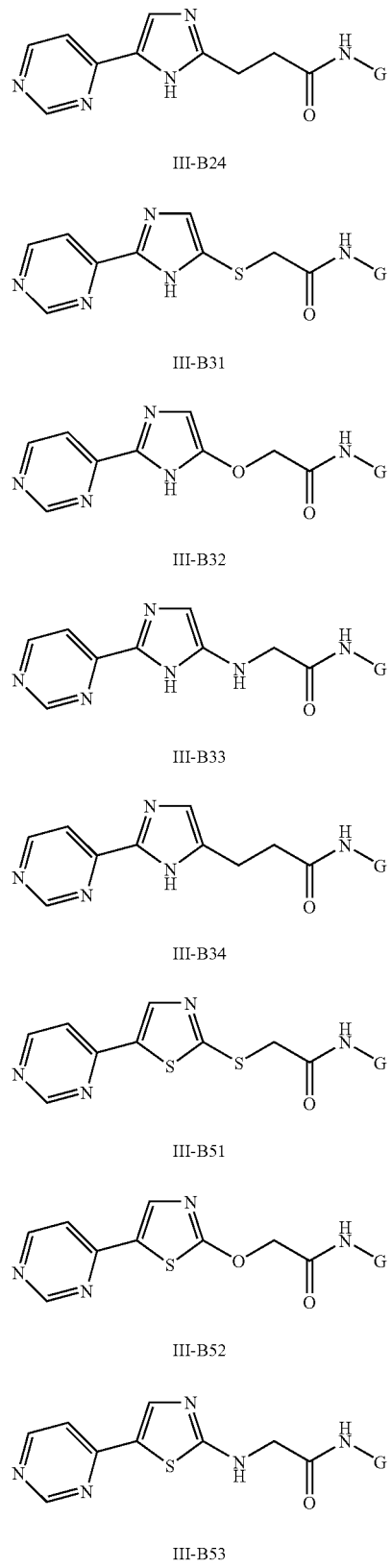

TABLE 1-continued

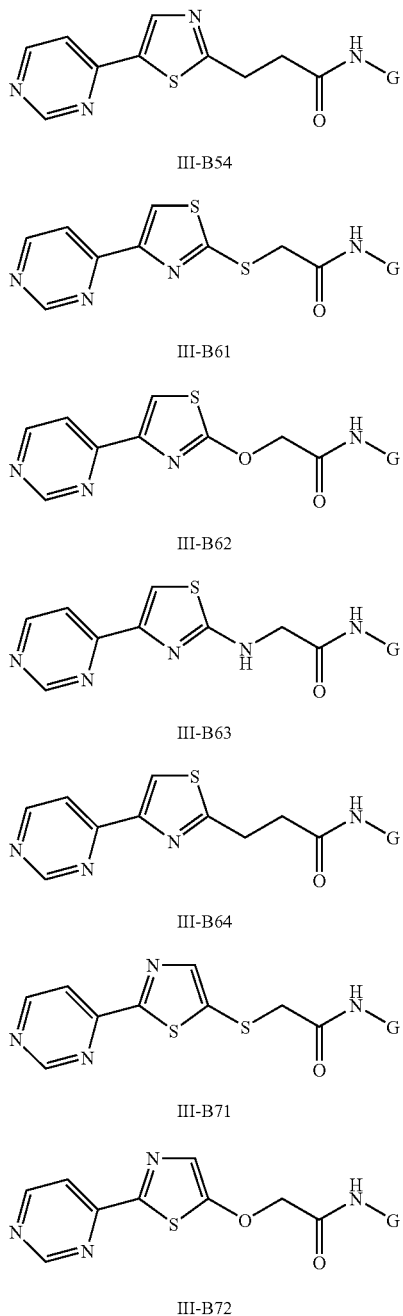

III-B54

III-B61

III-B62

III-B63

III-B64

III-B71

III-B72

TABLE 1-continued

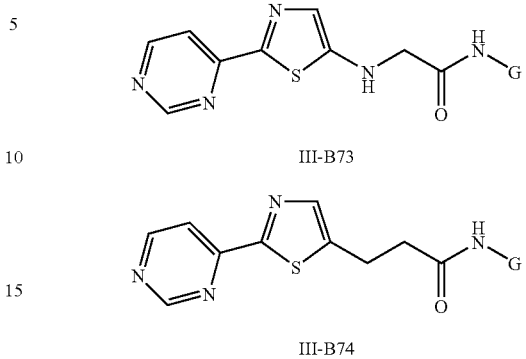

III-B73

III-B74

G is an aryl or heteroaryl ring that is optionally substituted by 1-4 $R^5$ groups. Preferred G are phenyl or pyridyl rings. $R^5$ is —$R^6$, -Q-$R^6$, or —V-Q-$R^6$.

Q is preferably a $C_{1-5}$ alkylidene, more preferably $C_{2-4}$ alkylidene.

V is preferably —O—, —C(O)—, or —NH—.

$R^6$ is preferably halo, $C_{1-6}$ alkyl, $C_{1-6}$ alkoxy, $C_{1-6}$ haloalkyl, $C_{1-6}$ haloalkoxy, amino, mono- or dialkylamino, mono- or dialkylaminocarbonyl, $C_{2-6}$ alkylcarbonyl, $C_{2-10}$ alkoxycarbonyl, $C_{2-10}$ alkoxycarbonylamino, $C_{2-6}$ alkylcarbonylamino, $C_{2-6}$ alkylsulfonylamino, $C_{2-6}$ mono- or dialkylaminosulfonyl, cyano, phenyl, 5-6 membered heterocyclyl or two adjacent $R^6$ groups taken together with their intervening atoms form a fused 5-6 membered, unsaturated or partially unsaturated ring having 0-2 ring heteroatoms selected from N, O, or S. Examples of $R^6$ include chloro, fluoro, bromo, methoxy, methyl, cyano, dimethylamino, trifluoromethyl, hydroxy, N-morpholinyl, N-piperidinyl, N-pyrrolidinyl, and N-piperazinyl.

Representative compounds of this invention are shown in Table 2.

TABLE 2

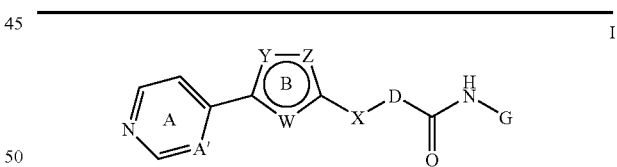

I

Ring B is selected from:

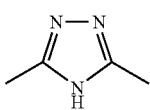

b-1

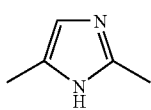

b-2

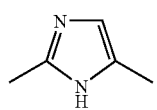

b-3

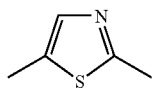

b-5

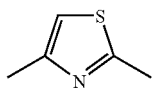

b-6

| Cmpd. No. | A' | Ring B | X | D | G |
|---|---|---|---|---|---|
| I-1 | CH | b-2 | S | CH$_2$ | phenyl |
| I-2 | CH | b-2 | S | CH$_2$ | 3-Cl-phenyl |
| I-3 | CH | b-2 | S | CH(CH$_3$) | 3-Cl-phenyl |
| I-4 | N | b-2 | S | CH$_2$ | 3-Cl-phenyl |
| I-5 | CH | b-2 | SO$_2$ | CH$_2$ | 3-Cl-phenyl |
| I-6 | CH | b-2 | SO | CH$_2$ | 3-Cl-phenyl |
| I-7 | CH | b-2 | S | CH$_2$ | 1-naphthyl |
| I-8 | CH | b-2 | CH$_2$ | CH$_2$ | 3-Cl-phenyl |
| I-9 | CH | b-2 | CH$_2$ | CH$_2$ | 3,5-Cl$_2$-phenyl |
| I-10 | CH | b-2 | S | CH$_2$ | 2-Cl-phenyl |
| I-11 | CH | b-2 | S | CH$_2$ | 4-Cl-phenyl |
| I-12 | CH | b-2 | S | CH$_2$ | 3-OMe-phenyl |
| I-13 | CH | b-2 | S | CH$_2$ | 3-NO$_2$-phenyl |
| I-14 | CH | b-2 | S | CH$_2$ | 3-NH$_2$-phenyl |
| I-15 | CH | b-2 | S | CH$_2$ | 3-N(CH$_3$)$_2$-phenyl |
| I-16 | CH | b-2 | S | CH$_2$ | 3-CH$_3$-phenyl |
| I-17 | CH | b-2 | S | CH$_2$CH$_2$ | 3-CH$_3$-phenyl |
| I-18 | CH | b-2 | S | CH$_2$ | 3-F-phenyl |
| I-19 | CH | b-2 | S | CH$_2$ | 3-Br-phenyl |
| I-20 | CH | b-2 | S | CH$_2$ | 3-CF$_3$-phenyl |
| I-21 | CH | b-2 | NH | CH$_2$ | 3-Cl-phenyl |
| I-22 | CH | b-2 | NH | CH$_2$ | 3-F-phenyl |
| I-23 | CH | b-2 | NH | CH$_2$ | 3-CH$_3$-phenyl |
| I-24 | CH | b-2 | NH | CH$_2$ | 3-OCH$_3$-phenyl |
| I-25 | CH | b-2 | O | CH$_2$ | 3-Cl-phenyl |
| I-26 | CH | b-2 | O | CH$_2$ | 3-F-phenyl |
| I-27 | CH | b-2 | O | CH$_2$ | 3-CH$_3$-phenyl |
| I-28 | CH | b-2 | O | CH$_2$ | 3-OCH$_3$-phenyl |
| I-29 | CH | b-1 | S | CH$_2$ | 3-Cl-phenyl |
| I-30 | CH | b-1 | S | CH$_2$ | 3-F-phenyl |
| I-31 | CH | b-1 | S | CH$_2$ | 3-Br-phenyl |
| I-32 | CH | b-1 | S | CH$_2$ | 3-CF$_3$-phenyl |
| I-33 | CH | b-1 | S | CH$_2$ | 3,5-Cl$_2$-phenyl |
| I-34 | CH | b-1 | S | CH$_2$ | 2-Cl-phenyl |
| I-35 | CH | b-1 | S | CH$_2$ | 4-Cl-phenyl |
| I-36 | CH | b-1 | S | CH$_2$ | 3-OCH$_3$-phenyl |
| I-37 | CH | b-1 | S | CH$_2$ | 3-NO$_2$-phenyl |
| I-38 | CH | b-1 | S | CH$_2$ | 3-NH$_2$-phenyl |
| I-39 | CH | b-1 | S | CH$_2$ | 3-N(CH$_3$)$_2$-phenyl |
| I-40 | CH | b-1 | S | CH$_2$ | 3-CH$_3$-phenyl |
| I-41 | CH | b-1 | S | CH$_2$ | phenyl |
| I-42 | CH | b-1 | CH$_2$ | C(CH$_3$)$_2$ | phenyl |
| I-43 | CH | b-1 | S | CH$_2$ | phenyl |
| I-44 | N | b-1 | S | CH$_2$ | 3-Cl-phenyl |
| I-45 | CH | b-1 | SO$_2$ | CH$_2$ | 3-Cl-phenyl |
| I-46 | CH | b-1 | SO | CH$_2$ | 3-Cl-phenyl |
| I-47 | CH | b-1 | SO$_2$ | CH$_2$CH$_2$ | 3-Cl-phenyl |
| I-48 | CH | b-1 | CH$_2$ | CH$_2$ | 3-Cl-phenyl |
| I-49 | CH | b-1 | NH | CH$_2$ | 3-Cl-phenyl |
| I-50 | CH | b-1 | NH | CH$_2$ | 3-F-phenyl |
| I-51 | CH | b-1 | NH | CH$_2$ | 3-CH$_3$-phenyl |
| I-52 | CH | b-1 | NH | CH$_2$ | 3-OCH$_3$-phenyl |
| I-53 | CH | b-1 | O | CH$_2$ | 3-Cl-phenyl |
| I-54 | CH | b-1 | O | CH$_2$ | 3-F-phenyl |
| I-55 | CH | b-1 | O | CH$_2$ | 3-CH$_3$-phenyl |
| I-56 | CH | b-1 | O | CH$_2$ | 3-OCH$_3$-phenyl |
| I-57 | CH | b-1 | S | CH$_2$ | 3-OH-phenyl |
| I-58 | CH | b-1 | S | CH$_2$ | 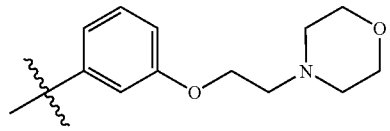 |
| I-59 | CH | b-1 | S | CH$_2$ | 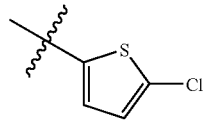 |

| | | | | |
|---|---|---|---|---|
| I-60 | CH | b-1 | S | CH$_2$ | 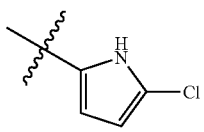 |
| I-61 | CH | b-1 | S | CH$_2$ | 2-pyridyl |
| I-62 | CH | b-1 | S | CH$_2$ | 3-pyridyl |
| I-63 | CH | b-1 | S | CH$_2$ | 4-pyridyl |
| I-64 | CH | b-1 | S | CH$_2$ | 6-Cl-indol-2-yl |
| I-65 | CH | b-3 | S | CH$_2$ | 3-Cl-phenyl |
| I-66 | CH | b-3 | S | CH$_2$ | 3-Cl-phenyl |
| I-67 | CH | b-2 | CH$_2$ | SCH$_2$ | 3-Cl-phenyl |
| I-68 | CH | b-2 | CH$_2$ | OCH$_2$ | 3-Cl-phenyl |
| I-69 | CH | b-2 | CH$_2$ | SCH$_2$ | 3-Ac-phenyl |
| I-70 | CH | b-2 | CH$_2$ | SCH$_2$ | 3-Cl-4-NMe$_2$-phenyl |
| I-71 | N | b-2 | CH$_2$ | SCH$_2$ | 3-Cl-4-NMe$_2$-phenyl |
| I-72 | CH | b-5 | CH$_2$ | SCH$_2$ | 3-Cl-phenyl |
| I-73 | N | b-5 | CH$_2$ | SCH$_2$ | 3-Cl-phenyl |
| I-74 | CH | b-5 | CH$_2$ | SCH$_2$ | 3-OCH$_3$-phenyl |
| I-75 | N | b-5 | CH$_2$ | SCH$_2$ | 3-OCH$_3$-phenyl |
| I-76 | CH | b-6 | CH$_2$ | SCH$_2$ | 3-Cl-phenyl |
| I-77 | CH | b-1 | CH$_2$ | SCH$_2$ | cyclohexyl |

Some of the compounds that are useful for treating a patient having a TGF-β mediated disorder are novel. One embodiment of this invention provides compounds represented by formula V:

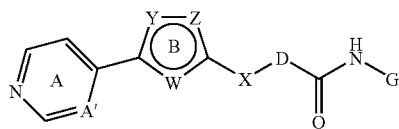

or a pharmaceutically acceptable salt thereof, wherein:

A' is N or CH;

Ring A is optionally substituted by 1-3 R$^1$;

Ring B is a heteroaryl ring that is optionally substituted at a substitutable nitrogen by R$^3$ and optionally substituted at a substitutable carbon by R$^{2a}$, wherein (i) W is NH, Z is CH, and Y is N, (ii) W is CH, Z is NH, and Y is N, (iii) W is S, Z is N, and Y is CH, (iv) W is S, Z is N, and Y is N, (v) W is N, Z is S, and Y is CH, or (vi) W is S, Z is CH, and Y is N;

—X-D- is a linker group having a length of about 300 to 900 picometers;

G is an aryl or heteroaryl ring that is optionally substituted by 1-4 R$^5$;

Each R$^1$ is independently selected from —R$^2$, -T-R$^2$, or —V-T-R$^2$;

Each R$^2$ is independently selected from C$_{1-3}$ aliphatic, hydroxy, —N(R$^3$)$_2$, halo, cyano, —OR$^4$, —C(O)R$^4$, —CO$_2$R$^4$, —SR$^4$, —S(O)R$^4$, —SO$_2$R$^4$, —N(R$^3$)C(O)R$^4$, —N(R$^3$)CO$_2$R$^4$, —N(R$^3$)SO$_2$R$^4$, —C(O)N(R$^3$)$_2$, —SO2N(R$^3$)$_2$, —N(R$^3$)C(O)N(R$^3$)$^2$, —OC(O)R$^4$, phenyl, 5-6 membered heterocyclyl or 5-6 membered heteroaryl;

R$^{2a}$ is C$_{1-6}$ alkyl;

Each T is independently a C$_{1-5}$ alkylidene that is optionally interrupted by —O—, —C(O)—, —S—, —S(O)—, —SO$_2$—, or —N(R$^3$)—;

Each V is independently selected from —O—, —S—, —S(O)—, —SO$_2$—, —C(O)—, —N(R$^3$)—, —N(R$^3$)C(O)—, or —N(R$^3$)CO$_2$—, —N(R$^3$)SO$_2$—, —C(O)N(R$^3$)—, —SO$_2$N(R$^3$)—, —N(R$^3$)C(O)N(R$^3$)—, or —OC(O)—;

Each R$^3$ is independently selected from hydrogen, C$_{1-6}$ aliphatic, —C(O)R$^4$, —CO$_2$R$^4$, —SO$_2$R$^4$, or two R$^3$ on the same nitrogen together with their intervening nitrogen form a 5-6 membered heterocyclyl or heteroaryl ring having 1-3 ring heteroatoms selected from N, O, or S;

R$^4$ is a C$_{1-6}$ aliphatic group;

Each R$^5$ is independently selected from —R$^6$, -Q-R$^6$, or —V-Q-R$^6$;

Each Q is independently a C$_{1-5}$ alkylidene that is optionally interrupted by —O—, —C(O)—, —S—, —S(O)—, —SO$_2$—, or —N(R$^3$)—; and Each R$^6$ is independently selected from C$_{1-3}$ aliphatic, hydroxy, —N(R$^3$)$_2$, halo, cyano, —OR$^4$, —C(O)R$^4$, —CO$_2$R$^4$, —SR$^4$, —S(O)R$^4$, —SO$_2$R$^4$, —N(R$^3$)C(O)R$^4$, or —N(R$^3$)CO$_2$R$^4$, —N(R$^3$)SO$_2$R$^4$, —C(O)N(R$^3$)$_2$, —SO$_2$N(R$^3$)$_2$, —N(R$^3$)C(O)N(R$^3$)$_2$, —OC(O)R$^4$, phenyl, 5-6 membered heterocyclyl or 5-6 membered heteroaryl.

The compounds of this invention may be prepared by methods known to those skilled in the art for analogous compounds, as illustrated by the general schemes below, and by reference to the preparative examples shown below.

Scheme I

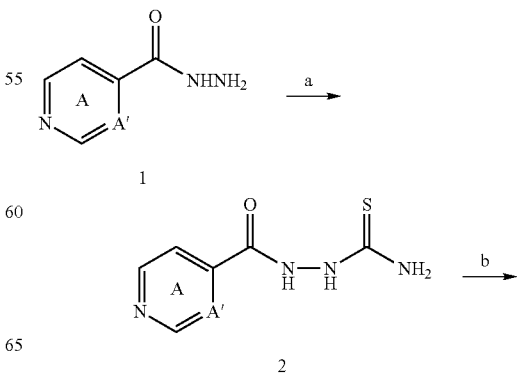

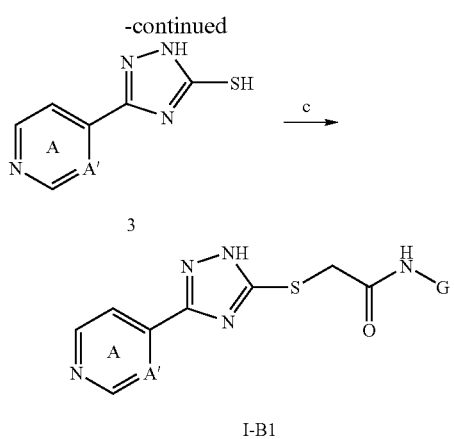

Reagents and conditions: (a) TMS-NCS, HOAc, 75° C.; (b) 2N NaOH, 100° C.; (c) ClCH$_2$C(O)NH-G, DMF Scheme I above describes a synthetic route for preparing compounds of the present invention where Ring B is a triazole ring. 5-Pyridin-4-yl-2H-[1,2,4]triazole-3-thiol (compound 3, A' is CH) and 5-pyrimidin-4-yl-2H-[1,2,4] triazole-3-thiol (compound 3, A' is N) are versatile intermediates. As shown in step (c), compound 3 may be coupled with 2-chloro-N-arylacetamides, such as a 2-chloro-N-phenylacetamide, to provide triazole compounds of the present invention. One skilled in the art would recognize that the general method of Scheme I may be used to prepare compounds where Ring A is substituted. Also, the chloroacetamide in step (c) may be replaced by other amides of the type haloalkyl-C(O)NH-aryl to provide triazoles having a longer linker group extending to the aryl or heteroaryl ring G.

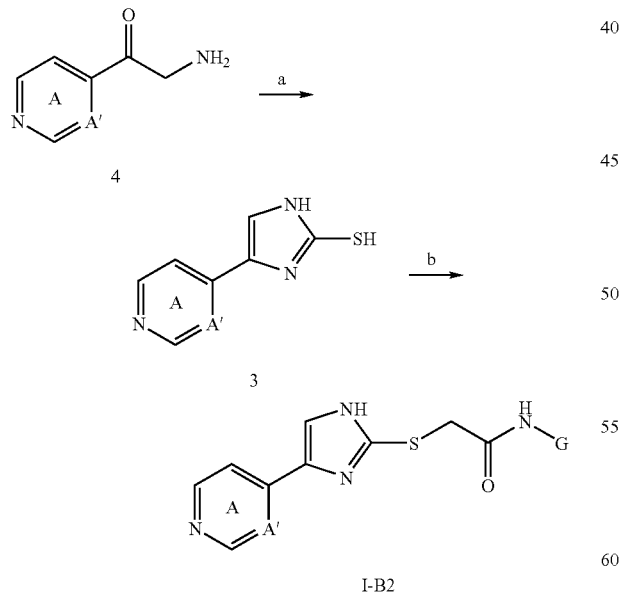

Reagents and conditions: (a) KSCN, H$_2$O, heat; (b) ClCH$_2$C(O)NH-G, CH$_2$Cl$_2$, Et$_3$N Scheme II above shows a general route for preparing imidazole compounds of the present invention. After the preparation of versatile intermediate 5, Scheme II is analogous to Scheme I above and may be used to prepare compounds having various G groups and substitutions on Ring A.

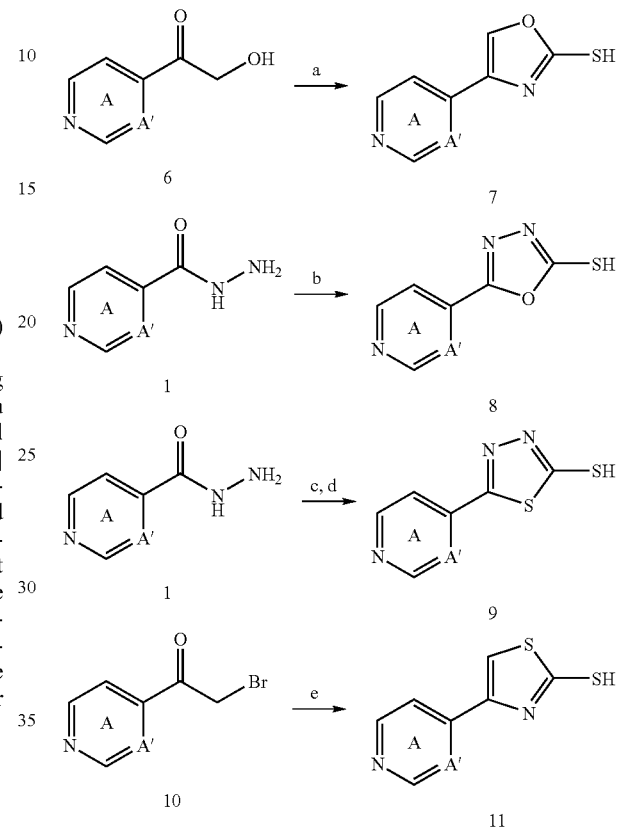

Reagents and conditions: (a) KSCN, concentrated HCl, 100° C.; (b) CS$_2$, KOH, EtOH, room temperature; (c) CS$_2$, KOH, EtOH, H$_2$O; (d) concentrated H$_2$SO$_4$; (e) H$_2$NCS$_2^-$NH$_4^+$, EtOH, room temperature; (f) 4—MeO—C$_6$H$_4$—CH$_2$—N=C=S; (g) refluxing aqueous NaOH Scheme III above shows a general route to obtain synthetic intermediates that are useful for making compounds of this invention where Ring B is an oxazole ring (compound 7), oxadiazole ring (compound 8), thiadiazole ring (compound 9), thiazole ring (compound 11), and triazole ring (compound 12). From each of these intermediates, the rest of the route is analogous to that shown in Scheme II above. The triazole intermediate 12 may be obtained from isonicotinic hydrazide (1, A' is CH) by reaction with p-methoxybenzyl isothiocyanate (PMB-NCS) in ethanol, isopropanol, or chlorobenzene with or without adding acetic acid. The resulting thiosemicarbazide derivative may be cyclized to 12 by refluxing in a suitable inorganic base such as aqueous sodium hydroxide or sodium bicarbonate. The para-methoxybenzyl group ("PMB") in 12 is a convenient protecting group that may be removed at a later step as described in Scheme IV. Other suitable protecting groups may be used in place of the PMB group.

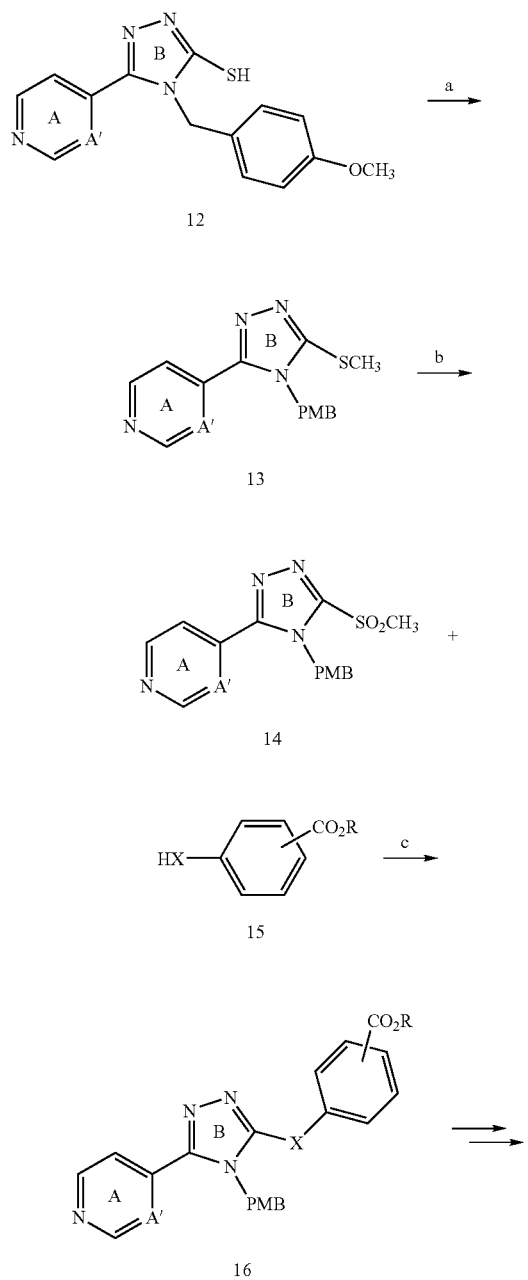

12

13

14

15

16

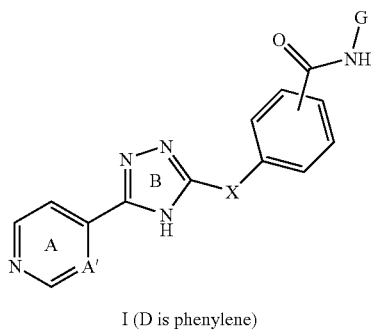

I (D is phenylene)

Scheme IV above shows a route to the present compounds wherein a phenyl ring provides the linker moiety connecting —CONH-G to Ring B, in this case a triazole ring. The starting triazole intermediate 12 may be treated with one equivalent of methyl iodide in acetonitrile, or methylene chloride, in the presence of a base, preferably, triethylamine, potassium carbonate, or cesium carbonate to afford a thiomethyl intermediate 13. Oxidation of 13 to the corresponding sulfone 14 may be accomplished with known oxidants such as m-chloro-perbenzoic acid, oxone, sodium metaperiodate, hydrogen peroxide, or potassium permanganate. The sulfone 14 may then be coupled with an appropriately substituted thiophenol (15, X is —S—), phenol (15, X is —O—),or aniline (15, X is —NH—) bearing a carboalkoxy group at an ortho-, meta-, or para-position. The coupling occurs in the presence of a base such as sodium hydride, potassium carbonate, or cesium carbonate, in either dimethylformamide, tetrahydrofuran, or acetonitrile. The resulting aryl esters 16 may then be derivatized to the corresponding amides I by known methods. For example, from 16 the amides may be formed in the presence of $G-NH_2$ using trimethyl aluminum in methylene chloride/hexane, or chloroform/toluene. Alternatively, the ester 16 may first be converted to the free carboxylic acid and then treated with $G-NH_2$ in the presence of peptide coupling reagents such as 1-(3-Dimethylaminopropyl)-3-ethylcarbodiimide (EDC) , dicyclohexylcarbodiimide (DCC), O-benzotriazol-1-yl)N, N,N',N'-tetramethyluronium hexafluorophosphate (HBTU), or benzotriazol-1yloxy-tris(dimethylamino)-phosphonium hexafluorophosphate (BOP). Finally, the coupled pyridinyltriazole anilides may be deprotected. If the protecting group is PMB, the group may be removed by treatment with trifluoroacetic acid in the presence of anisole, or by hydrogenolysis with hydrogen and a metal catalyst, preferably palladium on charcoal to provide compounds of the present invention where the linker is a substituted aryl ring.

Preferably, compounds of the present invention inhibit the phosphorylation of smad2 or smad3 by TGF-β type I or activin-like kinase (ALK)-5 receptor. The TGF-β inhibitory activity is useful in treating fibroproliferative diseases, treating collagen vascular disorders, treating eye diseases associated with a fibroproliferative condition, venting excessive scarring, treating neurological conditions and other conditions that are targets for TGF-β inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations. Neurological conditions characterized by TGF-β production include CNS injury after traumatic and hypoxic insults, Alzheimer's disease, and Parkinson's disease.

Other conditions that are potential clinical targets for TGF-β inhibitors include myelofibrosis, tissue thickening resulting from radiation treatment, nasal polyposis, polyp surgery, liver cirrhosis, and osteoporosis.

The phrase "TGF-β disease condition" includes those states, disorders, or diseases characterized by aberrant or undesirable activity or expression of TGF-β. Examples of TGF-β associated disease conditions include, but are not limited to, disorders involving or associated with cardiovascular diseases such as myocardial infarction, stroke, thrombosis, congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin, HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGF-β production or enhanced sensitivity to TGF-β, including states post-traumatic or hypoxic injury, Alzheimer's disease, and Parkinson's disease; and diseases of the joints involving scarring sufficient to impede mobility or produce pain, including states post-mechanical or surgical trauma, osteoarthritis and rheumatoid arthritis.

The modulation of the immune and inflammation systems by TGF-β includes stimulation of leukocyte recruitment, cytokine production, and lymphocyte effector function, and inhibition of T-cell subset proliferation, B-cell proliferation, antibody formation, and monocytic respiratory burst. Wahl et al., *Immunol Today* 10:258-61 (1989). TGF-β plays an important role in the pathogenesis of lung fibrosis which is a major cause of suffering and death seen in pulmonary medicine based upon its strong extracellular matrix inducing effect. The association of TGF-β with human lung fibrotic disorders has been demonstrated in idiophatic pulmonary fibrosis, autoimmune lung diseases and bleomycin induced lung fibrosis. Nakao et al., *J. Clin. Inv.*, 104(1):5-11 (1999).

TGF-β is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases.

TGF-β is also an important mediator of diabetic nephropathy, a common complication in patients with either type 1 or type 2 diabetes mellitus. Ziyadeh et al., *Proc.Natl. Acad.Sci.*, 97(14):8015-8020 (2000) evaluated the role of renal TGF-β in the development of chronic structural and functional changes of diabetic nephropathy by assessing the response of db/db mice to chronic treatment with neutralizing anti-TGF-β1 and generalized (tubular and glomerular) up-regulation of TGF-β type II receptor. The antibody effectively prevented increases in renal expression of matrix genes including type IV collagen and fibronectin and may have also stimulated matrix degradative pathways because TGF-β suppresses the activity of metalloproteinases and increase the expression of protease inhibitors such as plasminogen activator inhibitor-1 (PAI-1).

Other TGF-β disease states include inhibition of the intracellular signaling pathway such as fibroproliferative diseases, including kidney disorders associated with unregulated TGF-β activity and excessive fibrosis, including glomerulonephritis (GN), such as mesangial proliferative GN, immune GN, and crescentic GN. Other renal conditions which can be treated by inhibitors of TGF-β intracellular signaling pathway include diabetic nephropathy, renal interstitial fibrosis, renal fibrosis in transplant patients receiving cyclosporin, and HIV-associated nephropathy. Collagen vascular disorders which can be treated by inhibitors of TGF-β intracellular signaling pathway include progressive systemic sclerosis, polymyositis, scleroderma, dermnatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Eye diseases associated with a fibroproliferative condition include retinal reattachment surgery accompanying proliferative vitreoretinopathy, cataract extraction with intraocular lens implantation, and post glaucoma drainage surgery.

One embodiment of this invention relates to a method of treating or preventing chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, peritoneal and sub-dermal adhesion Another embodiment of this invention relates to the treatment of occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life threatening thrombi occurring throughout the microvasculature leading to widespread organ failure, hemmorhagic stroke, renal dialysis, blood oxygenation and cardiac catherization.

The compounds of this invention are also useful for coating stent devices. Stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention may be used for this purpose. Compounds of the invention may be attached to, or embedded within soluble and/or biodegradeable polymers that are suitable for coating a stent. Examples of such polymers include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

Compounds and pharmaceutical compositions suitable for use in the present invention include those wherein the active ingredient is administered in an effective amount to achieve its intended purpose. More specifically, a "therapeutically effective amount" means an amount effective to inhibit development of, or to alleviate the existing symptoms of, the subject being treated. Determination of the effective amount is well within the capability of those skilled in the art, especially in light of the detailed disclosure provided herein. A "therapeutically effective dose" refers to that amount of the compound that provides the desired effect. Toxicity and therapeutic efficacy of such compounds can be determined by standard pharmaceutical procedures in cell cultures or experimental animals, e. g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio of $LD_{50}$ to $ED_{50}$. Compounds that exhibit high therapeutic indices (i.e., a toxic dose that is substantially higher than the effective dose) are preferred. The data obtained can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized. The exact formulation, route of administration, and dosage is chosen by the individual physician in view of the patient's condition. Dosage amount and interval can be adjusted individually to provide plasma levels of the active compound that are sufficient to maintain desired therapeutic effects.

One embodiment of this invention relates to a composition comprising a compound of formula I or a pharmaceutically acceptable salt thereof, and a pharmaceutically acceptable carrier. It will be appreciated that the compounds of formula I in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula I, similar to the metabolically labile esters or carbamates, which are capable of producing the parent compounds of formula I in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers.

Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In order that this invention be more fully understood, the following preparative and testing examples are set forth. These examples are for the purpose of illustration only and are not to be construed as limiting the scope of the invention in any way.

SYNTHETIC EXAMPLES

Example 1

Preparation of N-(3-Chloro-phenyl)-2-(5-pyridin-3-yl-2H-[1,2,4]triazol-3-ylsulfanyl)-acetamide

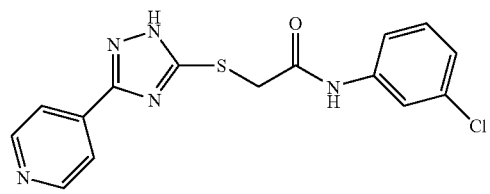

Step A: Preparation of the Thiosemicabazide Adduct of Nicotinic Acid

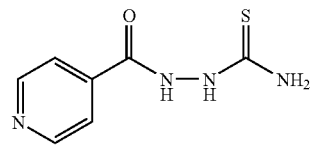

Isonicotinic acid hydrazide (1.06 g, 7.73 mmol) and trimethylsilyl isothiocyanate (2.03 g, 15.4 mmol) were dissolved in acetic acid (2.0 ml) in a round bottom flask with a condenser and stirred magnetically at 105° C. overnight. The solution was cooled to room temperature, at which time a solid formed. The acetic acid solution was decanted and any remaining solvent was evaporated with heating on a rotary evaporator. This residue was carried on as such to the next step.

Step B: Preparation of 5-pyridin-3-yl-2H-[1,2,4]triazole-3-thiol

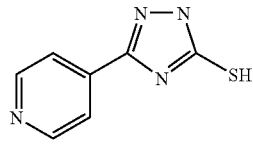

The thiosemicabazide adduct of nicotinic acid from Step A was dissolved in 5 N aqueous sodium hydroxide (5 ml) and heated to 95° C. for 6 hours, by which time the cyclization was complete as determined by HPLC and mass spectroscopy analysis. The solution was brought to pH 7 by the dropwise addition of concentrated hydrochloric acid. The compound precipitated out and was collected by filtration, rinsed with water and dried on a vacuum to yield pure title compound (546 mg, 40% yield)

Step C: Preparation of the Title Compound

The thiol intermediate prepared in Step B (101 mg, 0.567 mmol) was dissolved in DMF (2 ml) and triethylamine (0.24 ml, 1.7 mmol). 2,3'-dichloroacetanilide (116 mg, 0.567 mmol) was added and allowed to stir at room temperature overnight. The mixture was loaded directly onto an HPLC reverse phase column and purified by water to acetonitrile gradient in the presence of 0.1% trifluoroacetic acid. The aqueous phase was evaporated by lyophilization to yield the title compound as a fluffy white solid (166 mg, 85% yield). MS (ES) 346.5 (M+H)$^+$ Example 2

Preparation of N-(3-Chloro-phenyl)-2-(5-pyridin-3-yl-2H-[1,2,4]triazol-3-ylsulfinyl)-acetamide

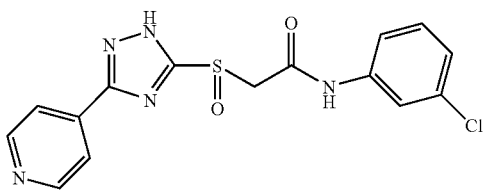

To a dichloromethane solution (2 mL) of N-(3-chloro-phenyl)-2-(5-pyridin-3-yl-2H-[1,2,4]triazol-3-ylsulfanyl)-acetamide (0.080 g, 0.25 mmol), m-chloroperbenzoic acid (0.25 mmol) was and the mixture was stirred for 2 h. The reaction mixture was quenched with sodium bicarbonate solution and the product extracted in ethyl acetate. The ethyl acetate layer was dried, filtered and evaporated to afford crude residue. This residue was purified by reverse phase HPLC to afford pure title compound (40 mg, 45%). MS (ES) 361.5

Example 3

Preparation of N-(3-chloro-phenyl)-2-(5-pyridin-3-yl-2H-[1,2,4]triazol-3-ylsulfonyl)-acetamide

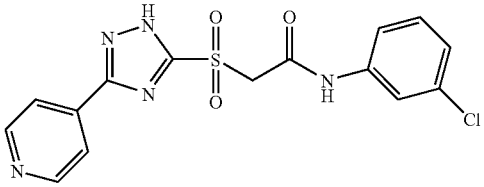

To a dichloromethane solution (2 mL) of N-(3-chloro-phenyl)-2-(5-pyridin-3-yl-2H-[1,2,4]triazol-3-ylsulfanyl)-acetamide (0.080 g, 0.25 mmol) added m-chloroperbenzoic acid (0.5 mmol) and reaction stirred for 2 h. The reaction was quenched with sodium bicarbonate solution and the product extracted in ethyl acetate. The ethyl acetate layer was dried, filtered and evaporated to afford crude residue. This was purified by reverse phase HPLC to afford pure title compound (55 mg, 52%). MS (ES) 378.5

Example 4

Preparation of N-(3-chlorophenyl)-2-(2-isopropyl-5-pyridin-4-yl-2H-[1,2,4]triazol-3-ylsulfanyl)-acetamide

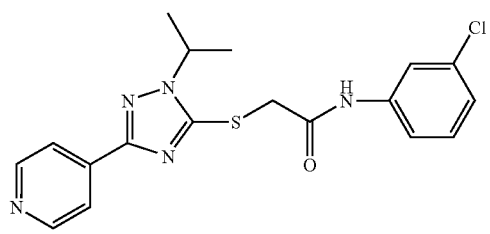

Step A: Synthesis of 2-isopropyl-5-pyridin-4-yl-2H-[1,2,4]-triazole-3-thiol

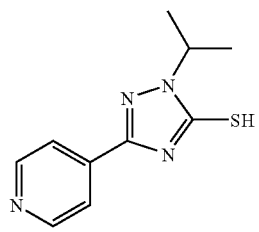

A mixture of IPRONIAZID (isonicotinic acid 2-isopropylhydrazide as its phosphate salt; commercially available from Aldrich) (277 mg, 1.0 mmol), and trimethyl-isothiocyanate (140 mg, 1.066 mmol) in chlorobenzene (5.0 mL) was heated to 90° C. for about 6 h. Analysis of the reaction showed the formation of acyl-thiosemicarbazide. Then heating was continued to higher temperature, and the mixture was refluxed for about 2 h, thereby cyclizing the acyl-thiosemicarbazide to thiol. The crude product was purified by HPLC to afford 174 mg (79%) of the thiol as a yellow solid.

Step B: N-(3-Chloro-phenyl)-2-(2-isopropyl-5-pyridin-4-yl-2H-[1,2,4]-triazol-3-ylsulfanyl)-acetamide

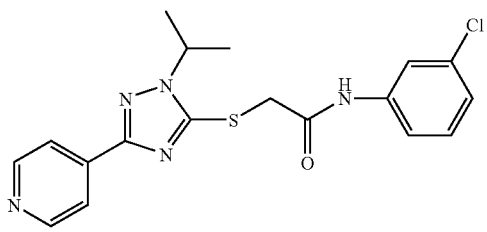

A mixture of the thiol TFA salt from Step A (100 mg, 0.30 mmol), N-(3-Chlorophenyl)-2-chloroacetamide (61 mg, 0.30 mmol), and triethylamine (0.145 mL 1.040 mmol) in dichloromethane (2.0 mL) was stirred at room temperature for 6 h. The solvent was removed by evaporation, and the crude product was purified by HPLC to afford the title compound as a colorless solid, 127 mg (85%). MS (ES): 388 (M+H)$^+$ Example 5

Preparation of N-(3-Chloro-phenyl)-2-(5-pyridin-3-yl-2H-[1,2,4]triazol-3-ylamino)-acetamide

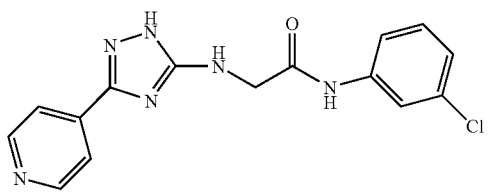

Step A: Preparation of 4-(5-methylsulfanyl-1H-[1,2,4]triazol-3-yl)-pyridine

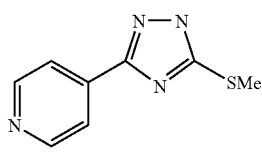

To a dichloromethane solution of 5-pyridin-3-yl-2H-[1,2,4]triazole-3-thiol (Step B, Example 1) triethylamine was added followed by iodomethane. This solution was stirred at room temperature for 2 h, during which period the reaction was complete by RP-HPLC. The solvent was evaporated and the residue was purified by RP-HPLC affording the desired intermediate.

Step B: Preparation of 4-(5-methylsulfanyl-1H-[1,2,4]triazol-3-yl)-pyridine

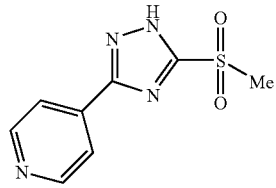

To a dichloromethane solution (2 mL) of product from step A (0.080 g, 0.25 mmol), m-chloroperbenzoic acid (0.50 mmol) was added and the reaction was stirred for 2 h. The reaction was quenched with sodium bicarbonate solution and the product extracted in ethyl acetate. The ethyl acetate layer was dried, filtered and evaporated to afford crude residue. This residue was purified by reverse phase HPLC to afford pure title compound Step C: Preparation of the Title Compound The sulfone from Step B (101 mg, 0.567 mmol) was dissolved in NMP (2 ml). To this solution 2-amino-N-(3-chlorophenyl)-acetamide (116 mg, 5 mmol) was added, and the mixture was heated at 140° C. for 12 h. The mixture was loaded directly onto an HPLC reverse phase column and purified by water to acetonitrile gradient in the presence of 0.1% trifluoroacetic acid. The aqueous phase was evaporated by lyophilization to yield the title compound as a fluffy white solid (166 mg, 85% yield). ES (MS): 345.12 (M+H)$^+$ Example 6

Preparation of N-(3-chlorophenyl)-3-(5-pyridin-4-yl-2H-[1,2,4]triazol-3-yl)-propionamide

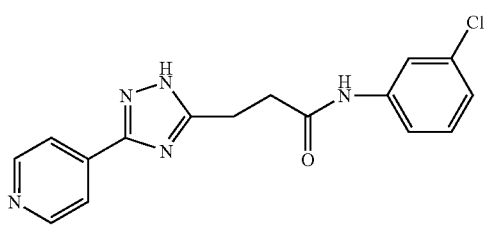

Step A: Preparation of N-(3-chlorophenyl)-3-hydrazinocarbonyl-propionamide

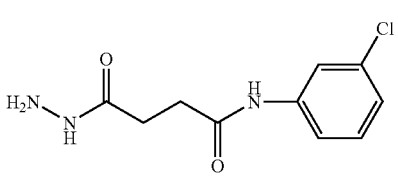

Succinic anhydride (10.0 g, 99.93 mmol) and 3-chloroaniline (12.80 g, 100.337 mmol) in DMF (75 mL) were heated to reflux for about 20 h. Then the DMF was removed in vacuo, and the crude product was triturated with ether (250 mL) to afford the title imide as a colorless solid, 12.8 g (61%).

The above imide (1.3 g, 6.19 mmol) in 1,4-dioxane (20 mL) was treated with anhydrous hydrazine (600 mg, 18.72 mmol), and the reaction mixture stirred at room temperature for 19 h. The mixture was then concentrated to dryness and triturated with ether to afford the title acyl hydrazide as a colorless solid, 1.46 g (98%).

Step B: Preparation of the Title Compound

4-Cyano-pyridine (300 mg, 2.88 mmol) in methanol (5 mL) was treated with sodium methoxide (15 mg, 0.277 mmol), and the clear reaction mixture stirred at room temperature for about 3 days. To this mixture was added the acyl-hydrazide from Step A (690 mg, 2.855 mmol). The reaction mixture was allowed to stand in the dark for about 5 days, during which time a colorless solid precipitate formed. The reaction mixture was concentrated to dryness to afford the title compound as a crude acyl-amidrazone.

The crude acyl-amidrazone was suspended in xylenes (5.0 mL), and heated to about 165° C. for about 3 h. Then the reaction was concentrated to dryness and purified by reverse-phase HPLC to afford the carbon analog, 438 mg (47%). MS (ES): 328 (M+H)

Example 7

Preparation of N-(3-chloro-phenyl)-2-(4-pyridin-4-yl-1H-imidazol-2-ylsulfanyl)-acetamide

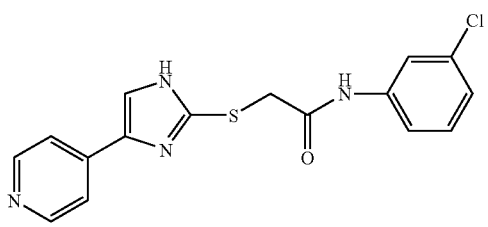

Step A: Preparation of 2-amino-1-pyridin-4-yl-ethanone

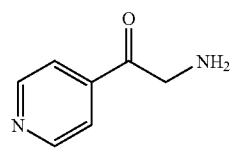

Sodium (700 mg, 30.43 mmol) was dissolved in anhydrous ethanol (75 ml) at room temperature. To this solution was added the 1-pyridin-4-yl-ethanone oxime (4.10 g, 30.14 mmol). After stirring at room temperature for 5 mins, p-toluene sulfonyl chloride (5.91 g, 31 mmol) was added as a solid and this was stirred for 1 h to generate the oxime tosylate in situ. Potassium metal (1.37 g, 35.03 mmol) was dissolved in anhydrous ethanol and to this mixture was added the solution of oxime tosylate. The mixture was stirred at room temperature for 4 hr and then filtered through a celite pad. The clear filtrate was concentrated to dryness and the residue re-dissolved in ether. The ether layer was washed with 2N HCl. The aqueous layer was basified and dried to yield the desired 2-amino-pyridine-4-yl-ethanone as a yellow solid.

Step B: Preparation of 4-Pyridin-4-yl-1H-imidazole-2-thiol

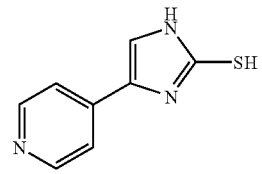

2-Amino-1-pyridin-4-yl-ethanone hydrochloride (0.75 g, 4.348 mMol) was dissolved in water (15 mL), and to clear yellow solution was added potassium thiocyanate (0.7 g, 7.203 mMol). The mixture was heated to reflux for 4.0 h during which period HPLC showed complete disappearance of starting material. On cooling to room temperature, a yellow solid precipitate formed, which was collected by filtration. The solid was then re-suspended in a saturated solution of NaHCO$_3$ (30 mL), stirred at room temperature for 0.5 h, and the resulting free base thiol was collected by filtration. The solid was dried under vacuum to yield 576 mg (59%) of a fluorescent yellow solid. MS(ES) 178 (M+H)

Step C: Synthesis of Title Compound

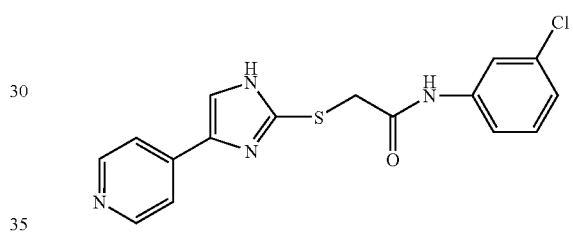

A mixture of thiol TFA salt from Step B (100 mg, 0.565 mMol), N-1-(3-chlorophenyl)-2-chloroacetamide (120 mg, 0.588 mmol), and triethylamine (0.30 mL 2.15 mmol), in dichloromethane (5.0 mL) was stirred at room temperature for 15 h. The solvent was removed in vacuo to provide the crude product, which was purified by HPLC to afford the title compound as a colorless solid, 159 mg (82%). MS (ES): 345 (M+H)

Example 8

N-(3-Chloro-phenyl)-2-(4-pyridin-4-yl-oxazol-2-ylsulfanyl)-acetamide

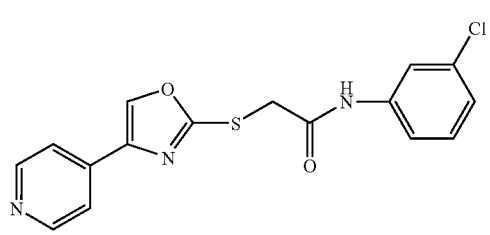

Pyridin-4-yl methanol (109 mg, 1 mmol) was treated with ethanolic potassium thiocyanate (0.125 g, 1.1 mmol) in presence of concentrated hydrochloride and heated to reflux for 6 h to afford 4-pyridin-4-yl-oxazole-2-thiol. A mixture of thiol HCl salt(100 mg, 1 mMol), N-1-(3-chlorophenyl)-2- chloroacetamide (240 mg, 1.17 mmol), and triethylamine (0.30 mL 2.15 mmol), in dichloromethane (5.0 mL) was stirred at room temperature for 15 h. The solvent was removed by evaporation, and the crude product was purified by HPLC to afford the title compound as a colorless solid, 250 mg (72%). MS (ES): 346 (M+H)+

Example 9

N-(3-Chloro-phenyl)-2-(4-pyridin-4-yl-oxazol-2-ylsulfanyl)-acetamide

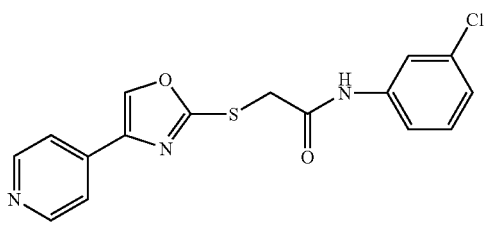

Pyridin-4-yl methanol was treated with ethanolic potassium thiocyanate in presence of concentrated hydrochloride and heated to afford 2-thiooxazole nucleus. The thiol was then coupled with N1-(3-chlorophenyl)-2-chloroacetamide as described before in methylene chloride, or acetonitrile in the presence of triethylamine to the title product.

Example 10

N-(3-Chloro-phenyl)-2-(5-pyridin-4-yl-[1,3,4]oxadiazol-2-ylsulfanyl)-acetamide

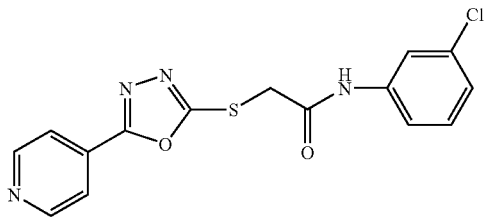

The commercially available 5-(4-Pyridyl)-1,3,4-oxadiazole (1 g, 5.58 mmol) was reacted with N1-(3-chlorophenyl)-2-chloroacetamide (1.25 g, 6.14 mmol) in acetonitrile in the presence of triethylamine (2.35 ml, 16.7 mmol) at room temperature for 3 hr. To this added ethyl acetate and washed with sodium bicarbonate solution and sodium chloride solution. The ethyl acetate layer was dried, filtered and evaporated to afford crude residue. This was purified by RP-HPLC to afford pure N-(3-Chloro-phenyl)-2-(5-pyridin-4-yl-[1,3,4]oxadiazol-2-ylsulfanyl)-acetamide (411 mg) as a light yellow solid. MS (ES): 347 (M+H)+

Example 11

N-(3-Chloro-phenyl)-2-(5-pyridin-4-yl-[1,3,4]thiadiazol-2-ylsulfanyl)-acetamide

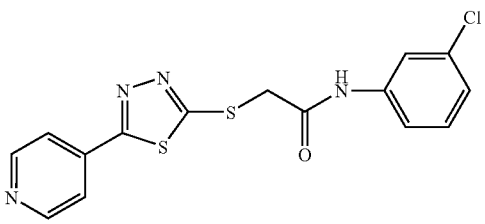

Isonicotinohydrazide (10.96 g, 79.9 mmol) was dissolved in ethanol (80 ml) containing potassium hydroxide (5.3 g, 94.4 mmol). Carbon disulfide was then added with stirring, which was continued for 1 hr. Filtration gave crude potassium 3-isonicotinoyldithiocarbazate which was washed with ether and then dried in vacuum. This was then added slowly with stirring to concentrated sulfuric acid (25 ml) maintained at −5° C. Stirring was continued for an additional 5 min and then the reaction mixture was poured into crushed ice. After 10 min, the solid was filtered off to give 5-(pyridine-4'yl)-1,3,4-thiadiazole-2(3H)-thione.

Step B: Synthesis of Title Compound

To the acetonitrile solution of thione/thiol (649 mg, 3.32 mmol) was added N1-(3-chlorophenyl)-2-chloroacetamide (713 mg, 3.49 mmol) in the presence of triethylamine (1.4 ml, 9.98 mmol) at room temperature for 3hr. The title compound was obtained as white solid after purification by reverse phase HPLC. MS (ES): 363 (M+H)+

Example 12

Preparation of N-(3-Chloro-phenyl)-2-(4-pyridin-4-yl-thiazol-2-ylsulfanyl)-acetamide

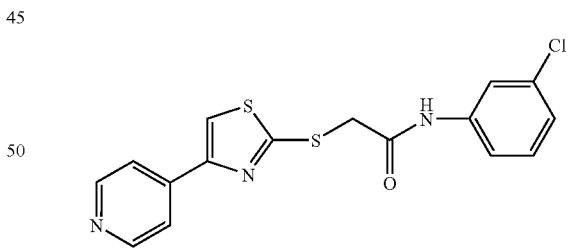

Ammonium dithiocarbamate (0.444 g, 4.03 mmol) was added to 2-bromo-1-(4-pyridinyl)-1-ethanone hydrobromide (1.03 g, 3.67 mmol) in ethanol (10 ml and stirring continued at room temperature for 18 hr. The solid was filtered and re-crystallized from methanol to give 4-pyridin-4-yl-thiazole-2-thiol. This thiol (272 mg, 1.39 mmol) was then coupled with N1-3-chlorophenyl)-2-chloroacetamide (284 mg, 1.39 mmol) as described in earlier examples, in acetonitrile in the presence of triethylamine (0.580 ml, 4.2 mmol) to afford crude product. This was purified by reverse phase HPLC to afford N-(3-Chloro-phenyl)-2-(4-pyridin-4-yl-thiazol-2-ylsulfanyl)-acetamide. MS (ES) 363 (M+H)+

Assay Methods

The following assay methods were used to evaluate the compounds of the present invention:

Autophosphorylation Assay of GST-ALK5

The cytoplasmic domain of ALK5 was fused to glutathione S-transferase (GST) and the GST-ALK5 fusion protein was expressed in a baculovirus expression system. GST-ALK5 was isolated with glutathione Sepharose 4B beads (Pharmacia Biotech, Sweden) and stored at −80° C. until use.

For detection of GST-ALK5 autophosphorylation and screening of inhibitory compounds, an aliquot of GST-ALK5 in 1× kinase buffer including [$^{33}$P]-γ-ATP was added to 96-well plates in the presence or absence of compounds. The mixture was then incubated at room temperature for 30 min and transferred to each well of a Filterplate with vacuum. The Filterplate was then washed 3 times and radioactivity in each well was counted in a Packard Top-Count.

In Vitro Kinase of HA-ALK5

An expression construct containing full-length ALK5 C-terminally tagged with HA was transfected into COS7 cells, and HA-ALK5 was isolated by immunoprecipitation with anti-HA antibodies. Aliquots of immunoprecipitated HA-ALK5 in 1× kinase buffer plus [$^{33}$p]-γ-ATP was added to 96-well plates in the presence or absence of different concentrations of testing compounds, and incubated at room temperature for 60 min. The reaction mixture was then transferred to a Filterplate. The plate was washed three times and radioactivity in each well counted. The $IC_{50}$ value for each compound was determined using the Prism3 program.

ELISA Assay for TGF-β Stimulated Smad2 Phosphorylation

Serum-starved normal human lung fibroblasts (NHLF) in 24-well plate were treated with or without different concentrations of testing compounds for 30 min. The cells were then stimulated with TGF-β for one hour. After fixing, permeabilizing, and blocking, the cells were incubated with phospho-Smad2 specific antibodies followed by HRP-conjugated secondary antibody. The extent of Smad2 phosphorylation was then detected using HRP substrate and read with an ELISA plate reader. $IC_{50}$ for each testing compound was determined using the PRISM3 program.

ELISA Assay for TGF-β Stimulated PAI-1 Secretion

Serum-starved NHLF in 24-well plates were treated with or without different concentrations of testing compounds for 30 min. The cells were then stimulated with TGF-β and incubated in a 37° C. incubator for 24 hours. The media were collected and added to 96-well plates coated with anti-PAI-1 antibodies. The secreted PAI-1 was then detected with another PAI-1 specific antibody followed by HRP-conjugated secondary antibody. The secretion of PAI-1 was detected using HRP substrate and read with an ELISA plate reader. $IC_{50}$ for each testing compound was determined using the PRISM3 program.

SIRCOL Collagen Assay for TGF-β Stimulated Cells

Serum-starved NHLF in 24-well plates were treated with or without different concentrations of testing compounds for 30 min. The cells were then stimulated with TGF-β and incubated for 24 hours. The media were collected and SIRCOL dye reagent was added. After spinning and washing, the pellets were resuspended in alkali reagent and read with an ELISA plate reader. The $IC_{50}$ value for each testing compound was determined using the PRISM3 program.

Detection of TGF-β Stimulated Fibronectin Expression

Serum-starved NHLF in 24-well plates were treated with or without different concentrations of testing compounds for 30 min. The cells were then stimulated with TGF-β and incubated for 24 hours. After washing and fixing, the secreted fibronectin was incubated with fibronectin specific antibodies, followed by incubation with biotin-labeled secondary antibody, streptavidin-peroxidase and HRP substrate. The signal was then detected using an ELISA reader. The $IC_{50}$ value for each testing compound was determined using the PRISM3 program.

The autophosphorylation of GST-ALK5 was developed for primary screening of the compounds that inhibit TGF-β signaling by interacting with ALK5. HA-ALK5 assay is a secondary screening assay to confirm the inhibitory compounds that were selected from the primary screening, and also for the determination of the $IC_{50}$ value for each compound.

P-Smad2, PAI-1, collagen and fibronectin assays are cell-based assays that are used for determination of functional activities of the compounds from the secondary screening. Since the molecules are targets of TGF-β signaling, the data demonstrated that the compounds specifically inhibit TGF-β mediated signal transduction.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

The invention claimed is:

1. A compound of formula V:

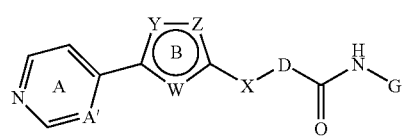

or a pharmaceutically acceptable salt thereof, wherein:

A' is N or CH;

Ring A is optionally substituted by 1-3 $R^1$;

Ring B is a heteroaryl ring that is optionally substituted at a substitutable nitrogen by $R^3$ and optionally substituted at a substitutable carbon by $R^{2a}$, wherein (i) W is NH, Z is CH, and Y is N, (ii) W is CH, Z is NH, and Y is N, (iii) W is S, Z is N, and Y is CH, (iv) W is S, Z is N, and Y is N, (v) W is N, Z is S, and Y is CH, or (vi) W is S, Z is CH, and Y is N;

X is —NH—, —O—, —CH$_2$— or —S—;

D is $C_{1-3}$ alkylidene;

G is an aryl or heteroaryl ring that is optionally substituted by 1-4 $R^5$;

Each $R^1$ is independently selected from -$R^2$, -T-$R^2$, or —V-T-$R^2$;

Each $R^2$ is independently selected from $C_{1-3}$ aliphatic, hydroxy, —N($R^3$)$_2$, halo, cyano, —OR$^4$, —C(O)R$^4$, —CO$_2$R$^4$, —SR$^4$, —S(O)R$^4$, —SO$_2$R$^4$, —N(R$^3$)C(O) R$^4$, —N(R$^3$)CO$_2$R$^4$, —N(R$^3$)SO$_2$R$^4$, —C(O)N(R$^3$)$_2$, —SO2N(R$^3$)$_2$, —N(R$^3$)C(O)N(R$^3$)$_2$, —OC(O)R$^4$, phenyl, 5-6 membered heterocyclyl or 5-6 membered heteroaryl;

$R^{2a}$ is $C_{1-6}$ alkyl;

Each T is independently a $C_{1-5}$ alkylidene that is optionally interrupted by —O—, —C(O)—, —S—, —S(O)—, —SO$_2$—, or —N(R$^3$)—;

Each V is independently selected from —O—, —S—, —S(O)—, —SO$_2$—, —C(O)—, —N(R$^3$)—, —N(R$^3$)C(O)—, or —N(R$^3$)CO$_2$—, —N(R$^3$)SO$_2$—, —C(O)N(R$^3$)—, —SO$_2$N(R$^3$)—, —N(R$^3$)C(O)N(R$^3$)—, or —OC(O)—;

Each $R^3$ is independently selected from hydrogen, $C_{1-6}$ aliphatic, —C(O)R$^4$, —CO$_2$R$^4$, —SO$_2$R$^4$, or two R$^3$ on the same nitrogen together with their intervening nitrogen form a 5-6 membered heterocyclyl or heteroaryl ring having 1-3 ring heteroatoms selected from N, O, or S;

$R^4$ is a $C_{1-6}$ aliphatic group;

Each $R^5$ is independently selected from —R$^6$, -Q-R$^6$, or —V-Q-R$^6$;

Each Q is independently a $C_{1-5}$ alkylidene that is optionally interrupted by —O—, —C(O)—, —S—, —S(O)—, —SO$_2$—, or —N(R$^3$)—; and Each $R^6$ is independently selected from $C_{1-3}$ aliphatic, hydroxy, —N(R$^3$)$_2$, halo, cyano, —OR$^4$, —C(O)R$^4$, —CO$_2$R$^4$, —SR$^4$, —S(O)R$^4$, —SO$_2$R$^4$, —N(R$^3$)C(O)R$^4$, or —N(R$^3$)CO$_2$R$^4$, —N(R$^3$)SO$_2$R$^4$, —C(O)N(R$^3$)$_2$, —SO$_2$N(R$^3$)$_2$, —N(R$^3$)C(O)N(R$^3$)$_2$, —OC(O)R$^4$, phenyl, 5-6 membered heterocyclyl or 5-6 membered heteroaryl.

2. The compound of claim 1 wherein G is an optionally substituted phenyl ring.

3. The compound of claim 1 wherein A' is CH.

4. The compound of claim 3 wherein Ring B is selected from the group consisting of:

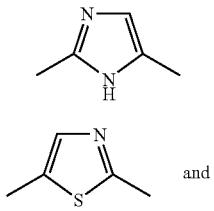

and

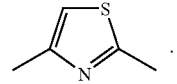

b-6

5. A pharmaceutical composition comprising a therapeutically effective amount of a compound of claim 1 and a pharmaceutically acceptable carrier.

6. A compound selected from the group consisting of:
N-(3-Chloro-phenyl)-2-(5-pyridin-3-yl-2H-[1,2,4]triazol-3-ylsulfanyl)-acetamide;
N-(3-Chloro-phenyl)-2-(5-pyridin-3-yl-2H-[1,2,4]triazol-3-ylsulfinyl)-acetamide;
N-(3-chloro-phenyl)-2-(5-pyridin-3-yl-2H-[1,2,4]triazol-3-ylsulfonyl)-acetamide;
N-(3-chlorophenyl)-2-(2-isopropyl-5-pyridin-4-yl-2H-[1,2,4]triazol-3-ylsulfanyl)-acetamide;
N-(3-Chloro-phenyl)-2-(5-pyridin-3-yl-2H-[1,2,4]triazol-3-ylamino)-acetamide;
N-(3-chlorophenyl)-3-(5-pyridin-4-yl-2H-[1,2,4]triazol-3-yl)-propionamide;
N-(3-chloro-phenyl)-2-(4-pyridin-4-1H-imidazol-2-ylsulfanyl)-acetamide;
N-(3-Chloro-phenyl)-2-(4-pyridin-4-yl-oxazol-2-ylsulfanyl)-acetamide;
N-(3-Chloro-phenyl)-2-(4-pyridin-4-yl-oxazol-2-ylsulfanyl)-acetamide;
N-(3-Chloro-phenyl)-2-(5-pyridin-4-yl-[1,3,4]triadiazol-2-ylsulfanyl)-acetamide; and
N-(3-Chloro-phenyl)-2-(4-pyridin-4-yl-thiazol-2-ylsulfanyl)-acetamide.

7. A pharmaceutical composition comprising a therapeutically effective amount of a compound of claim 6, and a pharmaceutically acceptable carrier.

* * * * *

UNITED STATES PATENT AND TRADEMARK OFFICE
CERTIFICATE OF CORRECTION

PATENT NO. : 7,361,669 B2
APPLICATION NO. : 10/747531
DATED : April 22, 2008
INVENTOR(S) : Robert M. Scarborough, Anjali Pandey and Mukund Mehrotra It is certified that error appears in the above-identified patent and that said Letters Patent is hereby corrected as shown below:

Please make the following corrections to the specification and claims:

SPECIFICATION

In column 3, line 51, change "-SO2N($R^3$)$_2$" to -- -SO$_2$N($R^3$)$_2$, --

In column 19, line 58, change "-SO2N($R^3$)$_2$" to -- -SO$_2$N($R^3$)$_2$, --

CLAIMS

In Claim 1, column 40, line 56, change "D is $C^{1-3}$ alkylidene;" to -- D is $C_{1-3}$ alkylidene; --

In Claim 1, column 40, line 65, change "-SO2N($R^3$)$_2$," to -- -SO$_2$N($R^3$)$_2$, --

Signed and Sealed this

Twentieth Day of January, 2009

JON W. DUDAS
*Director of the United States Patent and Trademark Office*